(12) United States Patent
Okui et al.

(10) Patent No.: US 9,902,806 B2
(45) Date of Patent: Feb. 27, 2018

(54) TRIOXANE COMPOSITION AND METHOD FOR STORING THE SAME

(71) Applicant: MITSUBISHI GAS CHEMICAL COMPANY, INC., Tokyo (JP)

(72) Inventors: Yumi Okui, Mie (JP); Daisuke Kobayashi, Mie (JP); Akira Ito, Mie (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/902,652

(22) PCT Filed: Jun. 30, 2014

(86) PCT No.: PCT/JP2014/067427
§ 371 (c)(1),
(2) Date: Jan. 4, 2016

(87) PCT Pub. No.: WO2015/005169
PCT Pub. Date: Jan. 15, 2015

(65) Prior Publication Data
US 2016/0168324 A1    Jun. 16, 2016

(30) Foreign Application Priority Data
Jul. 9, 2013  (JP) .................................. 2013-143759

(51) Int. Cl.
| C08G 59/00 | (2006.01) |
| C08G 65/16 | (2006.01) |
| C07D 323/06 | (2006.01) |
| C08G 2/10 | (2006.01) |
| C08G 2/24 | (2006.01) |
| C08L 59/04 | (2006.01) |

(52) U.S. Cl.
CPC ........... *C08G 65/16* (2013.01); *C07D 323/06* (2013.01); *C08G 2/10* (2013.01); *C08G 2/24* (2013.01); *C08L 59/04* (2013.01)

(58) Field of Classification Search
CPC .................................. C08G 2/10; C08G 4/00
See application file for complete search history.

(56) References Cited

U.S. PATENT DOCUMENTS

| 2,947,659 A * | 8/1960 | Rogers ................... A01N 25/04 106/501.1 |
| 3,519,650 A | 7/1970 | Fleck et al. |
| 4,579,935 A | 4/1986 | Kasuga et al. |
| 5,202,127 A | 4/1993 | Takeda et al. |
| 5,726,276 A * | 3/1998 | Nakai ...................... C08G 2/06 528/234 |
| 5,741,866 A | 4/1998 | Yahiro et al. |
| 6,048,892 A * | 4/2000 | Iwasaki ................ C07D 307/42 514/461 |
| 2009/0312466 A1* | 12/2009 | Hase ...................... C08K 5/005 524/100 |

FOREIGN PATENT DOCUMENTS

| CN | 1276372 | 12/2000 |
| JP | 53-130684 | 11/1978 |
| JP | 59-227916 | 12/1984 |
| JP | 63-115802 | 5/1988 |
| JP | 63-270604 | 11/1988 |
| JP | 6-135957 | 5/1994 |
| JP | 7-286023 | 10/1995 |
| JP | 2908693 | 4/1999 |
| JP | 11-269165 | 10/1999 |
| JP | 3134699 | 12/2000 |
| JP | 2011-137087 | 7/2011 |
| WO | 95/11892 | 5/1995 |
| WO | 2013/172270 | 11/2013 |

OTHER PUBLICATIONS

International Search Report issued is PCT/JP2014/067427, dated Sep. 9, 2014.
Partial Supplementary European Search Report issued in Patent Application No. 14823002.2, dated Feb. 7, 2017.
Chinese Search Report issued in Patent Application No. 2014800380348, dated Oct. 21, 2016.
Japanese Office Action issued in Counterpart Patent Appl. No. 2015-526275, dated Jul. 18, 2017, along with an english translation thereof.

\* cited by examiner

*Primary Examiner* — Shane Fang

(74) *Attorney, Agent, or Firm* — Greenblum & Bernstein, P.L.C.

(57) ABSTRACT

The present invention provides a trioxane composition which comprises trioxane as a main component, an antioxidant, and at least one alkaline organic compound selected from the group consisting of an amine compound having an alcoholic hydroxy group in the molecule thereof, a thiocarbamate compound, and an organophosphorus compound, wherein the amount of the alkaline organic compound contained is 0.01 to 10 ppm, based on the trioxane, and wherein the trioxane composition is a liquid.

11 Claims, No Drawings

TRIOXANE COMPOSITION AND METHOD FOR STORING THE SAME

FIELD OF THE INVENTION

The present invention relates to a trioxane composition and a method for storing the same.

BACKGROUND ART

A polyacetal resin, which is a type of engineering plastic, has, for example, excellent mechanical properties, sliding properties, frictional and abrasion properties, and chemical resistance, and has been used in a large amount as a key part for, for example, an automobile and an OA machine. It is considered that the amount of the polyacetal resin used will further increase worldwide year by year, and a further improvement of the production efficiency of the polyacetal resin is desired.

Various types of methods for producing a polyacetal resin have been known. For example, as a method for producing a polyacetal resin which is a copolymer, a general method includes the steps of: (1) producing formaldehyde using methanol as a raw material, (2) using an aqueous formaldehyde solution as a raw material, synthesizing trioxane which is to be used as a monomer, and further, for example, 1,3-dioxolane or 1,3-dioxepane which is to be used as a comonomer, and purifying the resultant products so as to have a high purity, (3) subjecting trioxane and the comonomer to polymerization reaction to synthesize a polyacetal resin, and then subjecting the synthesized resin and various additives added thereto to melting treatment to obtain product pellets, and (4) separating formaldehyde and trioxane from a dilute aqueous solution containing formaldehyde and trioxane discharged from the above steps and concentrating and recovering them using distillation or membrane separation.

Cyclic formals, such as trioxane and 1,3-dioxolane, are such unstable that they are likely to change in properties after being synthesized or purified, and they form peroxides and decomposition products, such as formaldehyde and formic acid, during the storage or transportation. The peroxides and decomposition products are disadvantageous not only in that they cause a lowering of the polymerization reaction rate in the synthesis of a polyacetal resin and a lowering of the quality of the obtained polyacetal resin, but also in that when they are formed in a large amount, insoluble paraformaldehyde may be formed and deposited. Deposition of paraformaldehyde clogs, for example, pipes and the inside of a distillation column, causing a severe problem in the stable production.

A technique has been disclosed in which crude trioxane formed in the course of obtaining high-purity trioxane is extracted with a water-insoluble inert organic solvent, and washed with an aqueous alkali solution, and then a specific tertiary amine is added to the resultant trioxane/water-insoluble inert organic solvent mixture, followed by distillation. By this technique, when trioxane is solidified and stored, or is repeatedly molten and solidified, the formation of white deposits from paraformaldehyde can be suppressed. The amount of the tertiary amine required in this technique is 0.01 to 10% by weight, based on the weight of the trioxane (see, for example, U.S. Pat. No. 3,519,650). On the other hand, a method has been disclosed in which, upon purifying crude trioxane by crystallization to obtain high-purity trioxane, an alkaline organic compound having a boiling point higher than that of trioxane is added (see, for example, Japanese Unexamined Patent Publication No. Hei 6-135957). All these methods are intended to suppress the formation of white deposits derived from paraformaldehyde when solidifying trioxane, and, for obtaining a satisfactory effect of by-product suppression, it is necessary to add an alkaline organic compound in such a high concentration that the polymerization reaction is terminated. For this reason, when the trioxane obtained by the above method is used in a polymerization reaction, the additives must be removed from the trioxane in advance so as not to inhibit the polymerization reaction.

Thus, in the conventional techniques, when trioxane in the form of a solid or flake is stored or transported, deposits derived from paraformaldehyde are caused unless an alkaline organic compound, such as a tertiary amine, in a large amount coexists with the trioxane, leading to severe problems, such as clogging of the facilities.

Further, in practice, trioxane is used in synthesizing a polyacetal resin and therefore preferably in a liquid state when being transferred to a reactor, and the trioxane in the form of a solid or flake needs much energy for heat melting and hence is not efficient. Further, a problem is encountered in the pollution caused in the step for pulverizing trioxane into a flake form. Accordingly, the trioxane obtained after synthesized or purified is preferably in a form such that the trioxane is stored or transported while maintaining the liquid state. In this connection, a method has been disclosed in which a predetermined antioxidant is added to trioxane to suppress deterioration with time caused due to the formation of impurities, such as a peroxide, formaldehyde, and formic acid, during the storage or transportation (see, for example, Japanese Patent Nos. 2908693 and 3134699). However, for example, Japanese Patent Nos. 2908693 and 3134699 have a description that the addition of an amine or phosphorus compound which terminates the polymerization reaction is inappropriate.

PRIOR ART REFERENCES

Patent Documents

Patent document 1: U.S. Pat. No. 3,519,650
Patent document 2: Japanese Unexamined Patent Publication No. Hei 6-135957
Patent document 3: Japanese Patent No. 2908693
Patent document 4: Japanese Patent No. 3134699

SUMMARY OF THE INVENTION

Problems to be Solved by the Invention

Only the addition of an antioxidant according to the conventional techniques is not always satisfactory in stabilization of the quality of trioxane being stored or transported, and a further improvement of the quality stabilization of trioxane has been desired. Accordingly, an object of the present invention is to provide a trioxane composition which can suppress the quality deterioration of trioxane to be used as a raw material for a polyacetal resin, and a method for storing the same.

Means to Solve the Problems

The present inventors have extensive and intensive studies with a view toward achieving the task of suppressing the quality deterioration of trioxane after being synthesized or purified. As a result, it has been found that a trioxane composition, which is obtained by adding an antioxidant and a specific alkaline organic compound to trioxane after being synthesized or purified, and which is a liquid, can suppress the quality deterioration of trioxane, and the present invention has been completed.

Specifically, the present invention encompasses the following embodiments.

(1) A trioxane composition including trioxane as a main component, an antioxidant, and at least one alkaline organic compound selected from the group consisting of an amine compound having an alcoholic hydroxy group in the molecule thereof, a thiocarbamate compound, and an organophosphorus compound, wherein the amount of the alkaline organic compound contained is 0.01 to 10 ppm, based on the trioxane, and wherein the trioxane composition is a liquid.

(2) The trioxane composition according to item (1) above, wherein the alkaline organic compound is at least one compound selected from the group consisting of a tertiary amine compound having an alcoholic hydroxy group in the molecule thereof, a dithiocarbamate compound, and an alkyl- or arylphosphine compound.

(3) The trioxane composition according to item (1) or (2) above, wherein the alkaline organic compound is triethanolamine.

(4) The trioxane composition according to any one of items (1) to (3) above, wherein the antioxidant is at least one compound selected from the group consisting of a phenolic compound and a hindered phenol compound; and wherein the amount of the antioxidant contained is 10 to 500 ppm, based on the trioxane.

(5) The trioxane composition according to any one of items (1) to (4) above, wherein the content of the trioxane in the trioxane composition, excluding the solvent, is 95% or more.

(6) A method for storing a trioxane composition, the method including maintaining the trioxane composition according to any one of items (1) to (5) above in a solution state or a molten liquid state.

(7) A polyacetal resin produced by polymerizing the trioxane composition according to any one of items (1) to (5) above.

Effect of the Invention

In the present invention, there can be provided a trioxane composition which can suppress the quality deterioration of trioxane to be used as a raw material for a polyacetal resin, and a method for storing the same.

EMBODIMENTS TO CARRY OUT THE INVENTION

In the present specification, the term "step" includes not only an independent step but also a step in which the anticipated effect of this step is achieved, even if the step cannot be clearly differentiated from the other steps. The range of values expressed using "to" indicates a range which includes the figures shown before and after "to" as, respectively, the minimum value and the maximum value. Further, with respect to the amount of a component contained in the composition, when a plurality of materials are present in the composition as the components of the composition, the amount of the components means the total amount of the materials present in the composition unless otherwise specified.

In the present specification, "ppm" is given by mass unless otherwise specified.

Further, the term "storage" of trioxane means storing trioxane in a container after being synthesized until it is used in producing a polyacetal resin, and examples of the containers for storage include a tank, a vessel, a container, and a drum, and the form of the container is not limited.

The trioxane composition of the present invention includes trioxane as a main component, an antioxidant, and at least one alkaline organic compound selected from the group consisting of an amine compound having an alcoholic hydroxy group in the molecule thereof, a thiocarbamate compound, and an organophosphorus compound, wherein the amount of the alkaline organic compound contained is 0.01 to 10 ppm, based on the trioxane, and wherein the trioxane composition is a liquid.

The trioxane composition can suppress the quality deterioration of trioxane being stored wherein the trioxane is a raw material for a polyacetal resin, and also can keep the state of the trioxane being stored during the transportation to suppress the quality deterioration of the trioxane being transported, enabling efficient and stable continuous production of the trioxane by a plant and achievement of stable quality of a polyacetal resin produced using the trioxane.

Further, with respect to crude trioxane containing a large amount of impurities obtained after being synthesized, or trioxane having a high purity obtained by purifying the crude trioxane using a purification means, such as distillation or membrane separation, for the purpose of using the resultant trioxane in producing a polyacetal resin, when the crude trioxane or high-purity trioxane is stored in a state such that it is maintained in a liquid state, i.e., in a solution state or a molten state and has added thereto both a specific antioxidant and a specific alkaline organic compound, the quality deterioration of the trioxane being stored can be more effectively suppressed.

Trioxane is a trimer of formaldehyde, and is a compound used as a monomer of a polyacetal resin which is of a homopolymer type or of a copolymer type. Crude trioxane synthesized using as a raw material an aqueous formaldehyde solution having a high concentration contains a large amount of water and other impurities. The crude trioxane is, if necessary, subjected to a step in which trioxane is extracted from the crude trioxane with an organic solvent unlikely to be soluble in or insoluble in water and obtained in the form of a uniform liquid mixture, and then the resultant liquid mixture is subjected to an operation, such as stepwise distillation or membrane separation, obtaining purified trioxane.

The trioxane composition contains trioxane as a main component. The wording "contains trioxane as a main component" means that the content of trioxane in the residue of the trioxane composition, which is obtained by removing the solvent from the trioxane composition, is 95% by mass or more, and the trioxane content is preferably 97% by mass or more, more preferably 99% by mass or more.

The form of the trioxane composition is a liquid which is any one of a state of a uniform solution obtained by dissolving trioxane in a solvent, and a molten state. The trioxane which can be used in the trioxane composition includes the all trioxane obtained in the process of from the synthesis thereof through the purification. In this case, for suppressing the quality deterioration of the trioxane, the trioxane composition having added thereto at least one antioxidant and the below-mentioned at least one alkaline organic compound in a concentration of 0.01 to 10 ppm is stored in a liquid state.

When the trioxane composition is in a solution state, there is no particular limitation with respect to the solvent for dissolving therein trioxane. The solvent is preferably one which is unlikely to be soluble in or insoluble in water and which forms a uniform liquid mixture together with trioxane, and more preferred is at least one member selected from the group consisting of aliphatic hydrocarbons, such as hexane, heptane, pentane, and cyclohexane; aromatic hydrocarbons, such as toluene and benzene; halogenated hydrocarbons, such as dichloroethane; and nitrobenzene. Of these, preferred are aromatic hydrocarbons in which trioxane exhibits high solubility, and which are easy to separate by utilizing a boiling point difference, and benzene is most preferably used. The solvents may be used individually or in combination.

The mass ratio of the solvent and trioxane may be appropriately selected depending on the temperature in the storing step and the solubility of trioxane in the solvent, and the solvent/trioxane mass ratio is, for example, 9/1 to 1/9, preferably 8/2 to 4/6.

With respect to the quality of trioxane to which an antioxidant and an alkaline organic compound are added, the purity of trioxane, excluding the solvent for dissolving therein trioxane, is preferably 97% by mass or more, more preferably 99% by mass or more. When the purity of the trioxane used for preparing the trioxane composition falls in this range, a satisfactory effect of suppressing the quality deterioration of trioxane due to the antioxidant and alkaline organic compound can be obtained, so that a satisfactory quality deterioration suppressing effect can be obtained by the addition of the antioxidant and alkaline organic compound in a further reduced amount.

The purified trioxane is trioxane having a purity increased by subjecting the trioxane after synthesized to stepwise purification step, and has a purity of higher than 99.5%, and further can have a purity of higher than 99.8%.

With respect to the temperature of the trioxane composition being stored, it is important to control the temperature by heating, retention, or cooling according to the state of the trioxane composition being stored. The upper limit of the temperature controlled is preferably a temperature lower than the boiling point of trioxane, or, when a solvent is used, the upper limit is preferably a temperature lower than the boiling point of trioxane or the solvent, any one of which has a lower boiling point than the other. For example, when the trioxane composition is in a state of a solution obtained by dissolving trioxane in benzene, the upper limit of the temperature controlled is, for example, lower than 80° C. which is the boiling point of benzene, and is preferably 70° C. or lower. Further, when using trioxane in a molten state, the upper limit of the temperature controlled is lower than 115° C., preferably 100° C. or lower. On the other hand, the lower limit of the temperature controlled is preferably a temperature higher than the freezing point of trioxane, or, when a solvent is used, the lower limit is preferably a temperature higher than the freezing point of trioxane or the solvent, any one of which has a higher freezing point than the other. For example, when the trioxane composition is in a state of a solution obtained by dissolving trioxane in benzene, the lower limit of the temperature controlled is preferably a temperature higher than about 5.5° C. which is the freezing point of benzene, preferably 10° C. or higher. Further, when using trioxane in a molten state, the lower limit of the temperature controlled is a temperature higher than 65° C., preferably 70° C. or higher.

The antioxidant contained in the trioxane composition is preferably a compound having a boiling point higher than that of trioxane. The antioxidant is preferably at least one member selected from the group consisting of a phenolic compound and a hindered phenol compound. Specific examples of antioxidants include phenolic compounds, such as phenol, cresol, and xylenol; and hindered phenol compounds, such as 2,6-di-tert-butyl-4-methylphenol, triethylene glycol-bis[3-(3-t-butyl-5-methyl-4-hydroxyphenyl) propionate], 1,6-hexanediol [3-(3,5-di-t-butyl-4-hydroxyphenyl) propionate], and pentaerythrityl-tetrakis[3-(3,5-di-t-butyl-4-hydroxyphenyl) propionate], and preferred is at least one compound selected from the group consisting of these compounds. As the antioxidant, particularly, for example, triethylene glycol-bis[3-(3-t-butyl-5-methyl-4-hydroxyphenyl) propionate] or pentaerythrityl-tetrakis[3-(3,5-di-t-butyl-4-hydroxyphenyl) propionate] is preferably used.

The antioxidants may be used individually or in combination.

The amount of the antioxidant contained in the trioxane composition is preferably the required amount or more, taking into consideration the conditions for and duration of the storage. For example, the amount of the antioxidant contained is 10 to 500 ppm, preferably 20 to 300 ppm, more preferably 30 to 200 ppm, based on the trioxane. When the amount of the antioxidant is 500 ppm or less, it is preferred from an economical point of view, and a problem, such as a lowering of the polymerization reaction rate or discoloration of the product due to decomposition products, does not occur in the synthesis of a polyacetal resin using the resultant trioxane composition.

The alkaline organic compound contained in the trioxane composition is at least one compound selected from the group consisting of an amine compound having an alcoholic hydroxy group in the molecule thereof, a thiocarbamate compound, and an organophosphorus compound. These compounds are organic compounds having a lone pair on the nitrogen atom or phosphorus atom which is an element belonging to Group 15 and being capable of becoming a proton acceptor. The alkaline organic compounds may be used individually or in combination.

The alcoholic hydroxy group indicates a hydroxyl group which is not bonded to the carbon of an aromatic ring.

The amine compound having an alcoholic hydroxy group in the molecule thereof (hereinafter, referred to simply as "amine compound") has an alcoholic hydroxy group portion and an amine portion. The amino group in the amine portion may be any of primary, secondary, and tertiary, and further may be any of an aliphatic amine, an aromatic amine, and a heterocyclic amine, and there is no particular limitation with respect to the structure of the amine. Examples of amine compounds include monoethanolamine, diethanolamine, triethanolamine, N-methylethanolamine, N,N-dimethylethanolamine, N-ethylethanolamine, N,N-diethylethanolamine, N-(β-aminoethypisopropanolamine, and hydroxyethylpiperazine, and preferred is at least one member selected from the group consisting of these compounds. Of these, a tertiary amine compound having an alcoholic hydroxyl group in the molecule thereof is more preferred, and examples of such compounds include triethanolamine, N,N-dimethylethanolamine, N,N-diethylethanolamine, and hydroxyethylpiperazine, and preferred is at least one compound selected from the group consisting of these compounds. Further, of these, a tertiary amine compound having two or more alcoholic hydroxy groups in the molecule thereof is especially preferred, and triethanolamine can be especially preferably used.

The amine compounds may be used individually or in combination.

The thiocarbamate compound includes zinc dimethyldithiocarbamate, zinc diethyldithiocarbamate, zinc dibutyldithiocarbamate, zinc ethylphenyldithiocarbamate, sodium dimethyldithiocarbamate, sodium diethyldithiocarbamate, copper dimethyldithiocarbamate, copper diethyldithiocarbamate, copper dibutyldithiocarbamate, iron dimethyldithiocarbamate, selenium diethyldithiocarbamate, nickel dibutyldithiocarbamate, tellurium diethyldithiocarbamate, and a dithiocarbamate compound (such as tetramethylthiuram disulfide), and at least one compound selected from the group consisting of these compounds is preferably used. Of these, at least one compound selected from the group consisting of dithiocarbamate compounds, such as zinc dimethyldithiocarbamate and sodium dimethyldithiocarbamate, and tetramethylthiuram disulfide is more preferably used, and a dithiocarbamate compound is especially preferably used.

The thiocarbamate compounds may be used individually or in combination.

Examples of organophosphorus compounds (referred to also as "phosphorus compound") include arylphosphine compounds, such as triphenylphosphine, and alkylphosphine compounds, such as tri-n-butylphosphine, and preferred is at least one compound selected from the group consisting of these compounds, and more preferred is at least one compound selected from the group consisting of arylphosphine compounds.

The organophosphorus compounds may be used individually or in combination.

The alkaline organic compound is preferably at least one compound selected from the group consisting of amine compounds having an alcoholic hydroxy group in the molecule thereof, such as triethanolamine, diethanolamine, monoethanolamine, N-methylethanolamine, N,N-dimethylethanolamine, N-ethylethanolamine, N,N-diethylethanolamine, N-(β-aminoethypisopropanolamine, and hydroxyethylpiperazine; thiocarbamate compounds, e.g., dithiocarbamate compounds, such as zinc dimethyldithiocarbamate and sodium dimethyldithiocarbamate, and tetramethylthiuram disulfide; and organophosphorus compounds, such as triphenylphosphine and tri-n-butylphosphine, more preferably at least one compound selected from the group consisting of a tertiary amine compound having an alcoholic hydroxy group in the molecule thereof, a dithiocarbamate compound, and an alkyl- or arylphosphine compound, further preferably at least one compound selected from the group consisting of triethanolamine, zinc dimethyldithiocarbamate, and triphenylphosphine.

The amount of the alkaline organic compound contained in the trioxane composition is preferably the required amount or more, taking into consideration the conditions for and duration of the storage, but the amount of the alkaline organic compound contained is 0.01 to 10 ppm, preferably 0.01 to 5 ppm, more preferably 0.1 to 5 ppm, based on the trioxane. When the amount of the alkaline organic compound is more than 10 ppm, it is not preferred from an economical point of view, and further a problem of a lowering of the polymerization reaction rate may occur in the synthesis of a polyacetal resin using the resultant trioxane composition.

With respect to the ratio of the antioxidant and alkaline organic compound contained in the trioxane composition, there is no particular limitation. From the viewpoint of suppressing a change of trioxane in properties, the ratio of the antioxidant to the alkaline organic compound (antioxidant/alkaline organic compound) is preferably 1 to 50,000, more preferably 2 to 5,000, further preferably 10 to 500.

In the trioxane composition, by adding an antioxidant in addition to an alkaline organic compound in a slight amount, excellent quality deterioration suppressing effect can be obtained. The reason for this is not clarified but is presumed to be due to a synergetic effect of the alkaline organic compound and the antioxidant.

A preferred embodiment of the trioxane composition is any one of the followings from the viewpoint of suppressing a change of trioxane in properties.

A1: the trioxane composition wherein the content of the trioxane in the trioxane composition, excluding the solvent, is 95% by mass or more, the amount of the contained at least one antioxidant selected from the group consisting of hindered phenol compounds is 10 to 500 ppm by mass, based on the trioxane, the amount of the contained alkaline organic compound selected from the group consisting of a tertiary amine compound having an alcoholic hydroxy group in the molecule thereof, a dithiocarbamate compound, and an alkyl- or arylphosphine compound is 0.01 to 10 ppm by mass, based on the trioxane, and the ratio of the antioxidant to the alkaline organic compound is 1 to 50,000.

A2: the trioxane composition wherein the content of the trioxane in the trioxane composition, excluding the solvent, is 99% by mass or more, the amount of the contained at least one antioxidant selected from the group consisting of hindered phenol compounds is 30 to 200 ppm by mass, based on the trioxane, the amount of the contained alkaline organic compound selected from the group consisting of a tertiary amine compound having an alcoholic hydroxy group in the molecule thereof, a dithiocarbamate compound, and an alkyl- or arylphosphine compound is 0.01 to 5 ppm by mass, based on the trioxane, and the ratio of the antioxidant to the alkaline organic compound is 2 to 5,000.

B1: the trioxane composition wherein the content of the trioxane in the trioxane composition, excluding the solvent, is 95% by mass or more, the amount of the contained at least one antioxidant selected from the group consisting of hindered phenol compounds is 10 to 500 ppm by mass, based on the trioxane, the amount of the contained alkaline organic compound selected from the group consisting of a tertiary amine compound having an alcoholic hydroxy group in the molecule thereof, a dithiocarbamate compound, and an alkyl- or arylphosphine compound is 0.01 to 10 ppm by mass, based on the trioxane, the ratio of the antioxidant to the alkaline organic compound is 1 to 50,000, and the mass ratio of the solvent and the trioxane, i.e., the solvent/trioxane mass ratio is 9/1 to 1/9.

B2: the trioxane composition wherein the content of the trioxane in the trioxane composition, excluding the solvent, is 99% by mass or more, the amount of the contained at least one antioxidant selected from the group consisting of hindered phenol compounds is 30 to 200 ppm by mass, based on the trioxane, the amount of the contained alkaline organic compound selected from the group consisting of a tertiary amine compound having an alcoholic hydroxy group in the molecule thereof, a dithiocarbamate compound, and an alkyl- or arylphosphine compound is 0.01 to 5 ppm by mass, based on the trioxane, the ratio of the antioxidant to the alkaline organic compound is 2 to 5,000, and the mass ratio of the solvent and the trioxane, i.e., the solvent/trioxane mass ratio is 8/2 to 4/6.

The trioxane composition is suppressed in the formation of formaldehyde, formic acid, and paraformaldehyde during the storage. For example, with respect to the trioxane composition obtained after being stored in a molten state, the formaldehyde content is, for example, 50 ppm or less, preferably 30 ppm or less. The formic acid content is, for example, less than 50 ppm, preferably less than 30 ppm. The paraformaldehyde content is, for example, less than 50 ppm, preferably less than 10 ppm.

The trioxane composition prevents trioxane to be used for producing a polyacetal resin from suffering a change in properties with the passage of time. Therefore, it is preferred that the addition of the antioxidant and alkaline organic compound is performed at any point of time in the process of from the synthesis of trioxane through the purification. With respect to the method for adding the antioxidant and alkaline organic compound, there is no particular limitation, and the antioxidant and the alkaline organic compound may be added individually to trioxane, or added in the form of a mixture thereof at one time. Further, they may be added in the form of a solution thereof. When added in the form of a solution, examples of solvents for the solution include water; aliphatic hydrocarbons, such as hexane, heptane, and cyclohexane; aromatic hydrocarbons, such as benzene, toluene, and xylene; and halogenated hydrocarbons, such as methylene dichloride and ethylene dichloride. The concentration of each of the antioxidant and alkaline organic compound in the solution can be arbitrarily determined, but, when added to trioxane having a high purity, the solvent can serve as an impurity, and therefore the concentration is preferably higher. When added to a trioxane solution, the same solvent as that for the trioxane solution may be used.

The trioxane composition can be obtained by a method which includes, for example, a step of providing trioxane, and a step of adding an antioxidant and at least one alkaline organic compound selected from the group consisting of an amine compound having an alcoholic hydroxy group in the molecule thereof, a thiocarbamate compound, and an organophosphorus compound to the provided trioxane so that the amount of the alkaline organic compound contained becomes 0.01 to 10 ppm, based on the trioxane, to obtain a trioxane composition.

The step of providing trioxane may be either a step of providing commercially available trioxane or a step of providing trioxane by producing it. Further, the step of providing trioxane may further include a step of purifying the trioxane if necessary.

The provided trioxane may be in a state of a solution obtained by dissolving the trioxane in a solvent, or in a molten state. The purity of the provided trioxane is, for example, in terms of a purity excluding the solvent, preferably 97% by mass or more, more preferably 99% by mass or more.

It is preferred that the trioxane composition is finally subjected to purification treatment for removing impurities including the solvent and then used in a synthesis of a polyacetal resin. As a purification treatment, distillation utilizing a boiling point difference is preferably performed especially for removing low boiling-point components, such as formaldehyde and water. In such a treatment, when an antioxidant and alkaline organic compound having a boiling point higher than the boiling point of trioxane are added, even if the purity of trioxane is increased to 99.9% or higher by distillation, the antioxidant and alkaline organic compound are still present in the trioxane composition after the distillation, suppressing the quality deterioration thereafter.

The method for storing a trioxane composition of the present invention includes maintaining the above-described trioxane composition in a liquid state, i.e., in a solution state or a molten state.

A preferred embodiment of the storing temperature for the trioxane composition is as already mentioned above.

With respect to the atmosphere for storing the trioxane composition, there is no particular limitation, and the atmosphere can be appropriately selected depending on, for example, the purpose. The atmosphere for storing the trioxane composition is preferably an inert gas atmosphere, such as a nitrogen atmosphere.

With respect to the pressure of the trioxane composition being stored, there is no particular limitation, and the pressure can be appropriately selected depending on, for example, the purpose. The pressure of the trioxane composition being stored is preferably atmospheric pressure to 0.5 MPa, more preferably 0.11 to 0.2 MPa.

With respect to the storing time for the trioxane composition, there is no particular limitation, and the storing time can be appropriately selected depending on, for example, the purpose. The storing time for the trioxane composition is, for example, preferably 0.1 hour or more, more preferably 10 hours or more. The upper limit of the storing time is, for example, 30 days or less, preferably 7 days or less.

The polyacetal resin of the present invention is produced by subjecting the above-mentioned trioxane composition to polymerization. That is, another embodiment of the present invention is the use of the trioxane composition in producing a polyacetal resin.

The polyacetal resin may be produced by directly subjecting the trioxane composition to polymerization, or may be produced by removing at least part of the solvent from the trioxane composition and then subjecting the resultant composition to polymerization. Further, the polyacetal resin may be a homopolymer produced by subjecting the trioxane composition to polymerization, or may be a copolymer produced by subjecting a mixture of the trioxane composition and a comonomer to polymerization.

The polyacetal resin is preferably one produced by subjecting the trioxane composition obtained after being stored as a raw material to polymerization.

EXAMPLES

Hereinbelow, the present invention will be described in more detail with reference to the following Examples, which should not be construed as limiting the scope of the present invention.

<Analytical Method for a Formaldehyde Content>

A formaldehyde content was measured by an acetylacetone colorimetry method. Ultrapure water was added to 1 g of trioxane in a molten state or an extraction water so that the resultant solution had a volume of 100 ml using a 100-ml measuring flask to form a sample solution. 10 ml of the formed sample solution, and 10 ml of a solution for colorimetry, which had been prepared by dissolving 4 ml of acetylacetone and 200 g of ammonium acetate in pure water and adding pure water thereto so that the resultant solution had a volume of 1 L, were mixed together and reacted with each other in a water bath at 60° C. for 10 minutes. After air-cooling in a dark room for one hour, an absorbance at 412 nm of the resultant sample was measured using UV-1800, manufactured by Shimadzu Corporation. Using an aqueous solution having a known formaldehyde concentration, a calibration curve was prepared in advance, and a formaldehyde concentration of the trioxane was calculated from the calibration curve.

With respect to only the trioxane composition in a solution state containing a solvent, an extraction water was prepared by a separation treatment in a separatory funnel using ultrapure water having the same mass as that of the trioxane composition.

<Analytical Method for a Formic Acid Content>

A formic acid content was measured by titration. 1 g of trioxane in a molten state or an extraction water was added to 100 ml of a solution obtained by adding 2 ml of 1/100 mol/L hydrochloric acid to 1 L of pure water. While stirring, the resultant mixture was subjected to titration with 1/100 mol/L NaOH using an automatic potentiometric titration apparatus, manufactured by Metrohm Japan Ltd. (716 DMS titrino), and a formic acid concentration of the trioxane was calculated from the resultant titration curve.

<Amount of the Paraformaldehyde Formed>

A glass filter was subjected to vacuum drying at 60° C. for one hour and then accurately weighed with the minimum scale of 0.001 g. The resultant glass filter was heated in a hot-air dryer to 80° C. at which the trioxane composition was not solidified, and the trioxane composition was subjected to filtration by means of suction using the glass filter before being cooled. Then, the trioxane composition deposited on the glass filter was quickly washed with acetone, and then the glass filter was subjected to vacuum drying at 60° C. for one hour and accurately weighed with the minimum scale of 0.001 g. A value obtained by dividing the increase of the mass of the glass filter by the mass of the trioxane composition subjected to filtration was determined as an amount of the paraformaldehyde formed.

<Polymerization Test>

Using, as a polymerization apparatus, a bench twin-shaft kneader having an inner capacity of 1 L and having a jacket and two Z-type blades, the trioxane composition was tested with respect to the polymerization reactivity by polymerization in a batch-wise manner. Hot water at 85° C. was circulated through the jacket, and further the inside of the apparatus was heated and dried using high-temperature air, and then a cover was attached to the apparatus and the system was purged with nitrogen. 320 g of the trioxane composition after being stored and 13 g of 1,3-dioxolane as a comonomer were charged through a raw material inlet, and, while stirring the resultant mixture by Z-type blades, 0.05 mmol of boron trifluoride diethyl etherate, relative to 1 mol of the trioxane, in the form of a benzene solution (solution concentration: 0.6 mmol/g) was added as a catalyst to the mixture to initiate a polymerization. After the polymerization was conducted for 900 seconds, a benzene solution (solution concentration: 5 mmol/ml) of triphenylphosphine in a molar amount corresponding to 10 times the molar amount of the catalyst used was added to the polymerization apparatus using a syringe, and mixed for 15 minutes to terminate the polymerization, obtaining a polyacetal resin.

In this instance, when the polymerization yield shown below was 80% or more, a rating "A" was given, and, when the polymerization yield was less than 80%, a rating "B" was given.

In Examples 1 to 3, the trioxane composition after being stored was subjected to distillation, and then the above-mentioned polymerization test was conducted with respect to the resultant composition.

<Polymerization Yield>

20 Grams of the polyacetal resin, which had been subjected to termination treatment, was immersed in 20 ml of acetone, and then subjected to filtration, and the collected resin was washed with acetone three times and then, subjected to vacuum drying at 60° C. until the weight of the dried resin became constant. Subsequently, the resultant resin was accurately weighed, and a polymerization yield was determined from the following formula.

Polymerization yield (%)=$M1/M0 \times 100$

M0: Weight before washing with acetone
M1: Weight after washing with acetone and drying Examples 1 to 3 and Comparative Example 1

To a uniform solution, which had been prepared from trioxane having a purity of 99.4% and containing water in an amount of 3,000 ppm, formaldehyde in an amount of 2,000 ppm, and formic acid in an amount of 20 ppm, and benzene in a (trioxane/benzene) ratio of 3/7, were added an antioxidant and an alkaline organic compound of the types and in the amounts shown in Table 1 to prepare a trioxane composition.

The obtained trioxane composition was placed in a closed container made of SUS 304 having therein a nitrogen atmosphere, and stored at 30° C. for 2 weeks. After storing, formaldehyde and formic acid were extracted with water from the resultant trioxane composition, and then a formaldehyde content and a formic acid content of the extraction water were measured by a colorimetry method and titration. Further, an amount of the paraformaldehyde formed was quantitatively determined.

Further, the trioxane composition obtained after being stored was subjected to distillation to obtain trioxane having a high purity, and then a polymerization test was conducted with respect to the obtained trioxane. The results are also shown in Table 1.

TABLE 1

|  |  | Example 1 | Example 2 | Example 3 | Comparative Example 1 |
|---|---|---|---|---|---|
| Antioxidant | Type | a-1 | a-1 | a-1 | — |
|  | Amount (ppm) | 50 | 50 | 51 | 0 |
| Alkaline organic compound | Type | b-1 | b-2 | b-3 | — |
|  | Amount (ppm) | 0.5 | 0.5 | 0.5 | 0 |
| Formaldehyde content after storage (ppm) |  | 2500 | 2700 | 2670 | 5000 |
| Formic acid content after storage (ppm) |  | 25 | 28 | 26 | 150 |
| Amount of paraformaldehyde formed (ppm) |  | ND | ND | ND | 360 |
| Operation of distillation purification |  | No problem | No problem | No problem | Clogged |
| Trioxane purity after distillation purification (%) |  | 99.9 | 99.9 | 99.9 | — |
| Formaldehyde content after distillation purification (ppm) |  | 24 | 31 | 41 | — |
| Formic acid content after distillation purification (ppm) |  | 11 | 17 | 19 | — |
| Polymerization test |  | A | A | A | — |

The abbreviations used in Table 1 have the following meanings.
Antioxidant:
a-1) Triethylene glycol-bis[3-(3-t-butyl-5-methyl-4-hydroxyphenyl) propionate] (trade name: IRGANOX 245; manufactured by BASF AG)
a-2) 1,6-Hexanediol-bis[3(3,5-di-t-butyl-4-hydroxyphenyl) propionate] (trade name: IRGANOX 259; manufactured by BASF AG)
Alkaline Organic Compound:
b-1) Triethanolamine
b-2) Triphenylphosphine
b-3) Zinc dimethyldithiocarbamate
Polymerization Test:
A: the polymerization yield is 80% or more, no problem occurs; B: the polymerization yield is less than 80%, the reaction rate or molecular weight is lowered.

Examples 4 to 8 and Comparative Examples 2 to 11

A uniform solution, which had been prepared from trioxane having a purity of 99.4% and containing water in an amount of 3,000 ppm, formaldehyde in an amount of 2,000 ppm, and formic acid in an amount of 20 ppm, and benzene in a ratio of 3/7, was subjected to distillation purification to obtain high-purity trioxane having a trioxane purity of 99.9% and containing formaldehyde and formic acid in respective amounts of 21 ppm and 9 ppm. To the resultant trioxane were added an antioxidant and an alkaline organic compound of the types and in the amounts shown in Tables 2 to 4 to prepare a trioxane composition.

The obtained trioxane composition was placed in a closed container made of SUS 304 having therein a nitrogen atmosphere, and stored at 80° C. for 20 days. After storing, a formaldehyde content and a formic acid content of the resultant trioxane composition were measured by a colorimetry method and titration. Further, an amount of the paraformaldehyde formed was quantitatively determined. Further, using the trioxane composition obtained after being stored, a polymerization test was conducted. The results are also shown in Tables 2 to 4.

TABLE 2

|  |  | Example 4 | Example 5 | Example 6 | Example 7 | Example 8 | Example 9 |
|---|---|---|---|---|---|---|---|
| Antioxidant | Type | a-1 | a-1 | a-2 | a-1 | a-1 | a-1 |
|  | Amount (ppm) | 50 | 150 | 150 | 50 | 50 | 50 |
| Alkaline organic compound | Type | b-1 | b-1 | b-1 | b-1 | b-5 | b-6 |
|  | Amount (ppm) | 0.5 | 0.5 | 0.5 | 5 | 0.5 | 0.5 |
| Formaldehyde content after storage (ppm) |  | 29 | 27 | 37 | 28 | 28 | 50 |
| Formic acid content after storage (ppm) |  | 27 | 26 | 28 | 26 | 29 | 31 |
| Amount of paraformaldehyde formed (ppm) |  | ND | ND | ND | ND | ND | ND |
| Polymerization test |  | A | A | A | A | A | A |

TABLE 3

|  |  | Comparative Example 2 | Comparative Example 3 | Comparative Example 4 | Comparative Example 5 | Comparative Example 6 | Comparative Example 7 |
|---|---|---|---|---|---|---|---|
| Antioxidant | Type | — | — | — | a-1 | a-1 | a-2 |
|  | Amount (ppm) | 0 | 0 | 0 | 150 | 1000 | 150 |
| Alkaline organic compound | Type | — | b-1 | b-1 | — | — | — |
|  | Amount (ppm) | 0 | 0.5 | 50 | 0 | 0 | 0 |
| Formaldehyde content after storage (ppm) |  | 500 | 480 | 470 | 60 | 60 | 120 |
| Formic acid content after storage (ppm) |  | 1900 | 1800 | 1750 | 50 | 50 | 45 |
| Amount of paraformaldehyde formed (ppm) |  | 39 | 26 | 17 | ND | ND | ND |
| Polymerization test |  | B | B | B | A | B | A |

TABLE 4

|  |  | Comparative Example 8 | Comparative Example 9 | Comparative Example 10 | Comparative Example 11 | Comparative Example 12 |
|---|---|---|---|---|---|---|
| Antioxidant | Type | a-1 | a-1 | a-1 | a-1 | a-1 |
|  | Amount (ppm) | 50 | 50 | 50 | 50 | 50 |
| Alkaline organic compound | Type | b-1 | b-1 | b-7 | b-8 | b-4 |
|  | Amount (ppm) | 20 | 50 | 0.5 | 0.5 | 0.5 |
| Formaldehyde content after storage (ppm) |  | 29 | 29 | 140 | 170 | 70 |
| Formic acid content after storage (ppm) |  | 23 | 22 | 170 | 190 | 150 |

TABLE 4-continued

|  | Comparative Example 8 | Comparative Example 9 | Comparative Example 10 | Comparative Example 11 | Comparative Example 12 |
|---|---|---|---|---|---|
| Amount of paraformaldehyde formed (ppm) | ND | ND | 27 | 31 | 16 |
| Polymerization test | B | B | A | A | A |

The abbreviations used in Tables 2 to 4 have the following meanings. Antioxidant:

a-1) Triethylene glycol-bis[3-(3-t-butyl-5-methyl-4-hydroxyphenyl) propionate] (trade name: IRGANOX 245; manufactured by BASF AG)

a-2) 1,6-Hexanediol-bis[3(3,5-di-t-butyl-4-hydroxyphenyl) propionate] (trade name: IRGANOX 259; manufactured by BASF AG)

Alkaline Organic Compound:
b-1) Triethanolamine
b-2) Triphenylphosphine
b-3) Zinc dimethyldithiocarbamate
b-4) Triethylamine
b-5) N,N-Diethylethanolamine
b-6) N-Ethyldiethanolamine
b-7) Bis(1,2,2,6,6-pentamethyl-4-piperidyl) cebacate
b-8) Polycondensation product of dimethyl succinate and 1-(2-hydroxyethyl)-4-hydroxy-2,2,6,6-tetramethyl-4-piperidine Polymerization Test:

A: the polymerization yield is 80% or more, no problem occurs; B: the polymerization yield is less than 80%, the reaction rate or molecular weight is lowered.

As can be seen from Tables 1 to 4, the trioxane composition of the present invention can effectively suppress the quality deterioration of trioxane during the storage, and can be advantageously applied to the production of a polyacetal resin.

The whole of the disclosure of Japanese Patent Application No. 2013-143759 is incorporated into the present specification by reference.

All the documents, patent applications, and technical standards described in the present specification are incorporated into the present specification by reference to the same extent as that in the case where it is specifically and individually shown that each of the documents, patent applications, and technical standards is incorporated into the present specification by reference.

The invention claimed is:

1. A polymerizable trioxane composition comprising trioxane as a main component, an antioxidant, and at least one alkaline organic compound selected from the group consisting of an amine compound having an alcoholic hydroxy group in the molecule thereof, a thiocarbamate compound, and an organophosphorus compound,
wherein the amount of the alkaline organic compound contained is 0.01 to 10 ppm, based on the trioxane, and
wherein the trioxane composition is a liquid which is a uniform solution of trioxane in an aromatic hydrocarbon solvent.

2. The trioxane composition according to claim 1, wherein the alkaline organic compound is at least one compound selected from the group consisting of a tertiary amine compound having an alcoholic hydroxy group in the molecule thereof, a dithiocarbamate compound, and an alkyl- or arylphosphine compound.

3. The trioxane composition according to claim 1, wherein the alkaline organic compound is triethanolamine.

4. The trioxane composition according to claim 1, wherein the antioxidant is at least one compound selected from the group consisting of a phenolic compound and a hindered phenol compound; and wherein the amount of the antioxidant contained is 10 to 500 ppm, based on the trioxane.

5. The trioxane composition according to claim 1, wherein the content of the trioxane in the trioxane composition, excluding the solvent, is 95% or more.

6. A method for storing a trioxane composition, the method comprising maintaining the trioxane composition according to claim 1 in a liquid state.

7. A method for storing a trioxane composition, the method comprising maintaining the trioxane composition according to claim 2 in a liquid state.

8. A method for storing a trioxane composition, the method comprising maintaining the trioxane composition according to claim 3 in a liquid state.

9. A method for storing a trioxane composition, the method comprising maintaining the trioxane composition according to claim 4 in a liquid state.

10. A method for storing a trioxane composition, the method comprising maintaining the trioxane composition according to claim 5 in a liquid state.

11. The trioxane composition of claim 1, wherein the aromatic hydrocarbon solvent is selected from the group consisting of benzene, toluene, xylene and mixtures thereof.

* * * * *